(12) United States Patent
Horton et al.

(10) Patent No.: US 10,980,592 B2
(45) Date of Patent: Apr. 20, 2021

(54) SKIN TREATMENT METHOD AND APPARATUS

(71) Applicant: KONINKLIJKE PHILIPS N.V., Eindhoven (NL)

(72) Inventors: Margaret Ruth Horton, Eindhoven (NL); Martin Jurna, Eindhoven (NL); Jonathan Alambra Palero, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1028 days.

(21) Appl. No.: 14/397,881

(22) PCT Filed: Jul. 9, 2013

(86) PCT No.: PCT/IB2013/055625
§ 371 (c)(1),
(2) Date: Oct. 30, 2014

(87) PCT Pub. No.: WO2014/009875
PCT Pub. Date: Jan. 16, 2014

(65) Prior Publication Data
US 2015/0133906 A1    May 14, 2015

Related U.S. Application Data

(60) Provisional application No. 61/669,187, filed on Jul. 9, 2012.

(51) Int. Cl.
*A61B 18/12* (2006.01)
*A61B 18/00* (2006.01)

(52) U.S. Cl.
CPC .... *A61B 18/12* (2013.01); *A61B 2018/00047* (2013.01); *A61B 2018/0047* (2013.01); *A61B 2018/00791* (2013.01)

(58) Field of Classification Search
CPC .......... A61B 18/12; A61B 2018/00047; A61B 2018/0047; A61B 2018/00791
See application file for complete search history.

(56) References Cited

U.S. PATENT DOCUMENTS 7,571,003 B2    8/2009   Pozzato
2003/0187488 A1*  10/2003   Kreindel ............ A61B 18/1402
                                                         607/101

(Continued)

FOREIGN PATENT DOCUMENTS

JP              4312472 A      11/1992
JP           2013543782 A      12/2013

(Continued)

OTHER PUBLICATIONS

R.S. Mullholland, "Radiofrequency Energy for Non-invasive and Minimally Invasive Skin Tightening", Clinics in Plastic Surgery, 38 (2011) 437-448.

*Primary Examiner* — Linda C Dvorak
*Assistant Examiner* — Tigist S Demie (57) ABSTRACT

A method of treating a skin tissue area (3) having a skin surface (5) is provided. The method comprises the steps of: deforming the skin tissue area into a deformed shape comprising a plurality of folds (17) in the skin tissue area; arranging radiofrequency electrodes (13) in contact with the skin surface on opposite sides of the deformed skin tissue area; and, while maintaining the skin tissue area in said deformed shape, providing a spatially continuous radiofrequency energy flow between the radiofrequency electrodes on opposite sides of the deformed skin tissue area through the deformed skin tissue area, thereby heating at least a portion (19) of the deformed skin tissue area; and releasing the skin tissue area from said deformed shape, thereby deforming said heated portion (19) into a wave-shaped zone of heated skin tissue having a depth relative to the skin (Continued)

surface that varies between a minimum and a maximum value in a direction between said opposite sides. Accordingly, an apparatus for treating a skin tissue area (3) is provided.

25 Claims, 8 Drawing Sheets

(56) References Cited

U.S. PATENT DOCUMENTS

| | | | |
|---|---|---|---|
| 2005/0049582 A1* | 3/2005 | DeBenedictis | A61B 18/20 606/9 |
| 2006/0036300 A1 | 2/2006 | Kreindel | |
| 2006/0047281 A1 | 3/2006 | Kreindel | |
| 2006/0074314 A1* | 4/2006 | Slayton | A61B 8/14 600/439 |
| 2009/0221938 A1 | 9/2009 | Rosenberg | |
| 2012/0046658 A1 | 2/2012 | Kreindel | |
| 2012/0116271 A1* | 5/2012 | Caruso | A61B 18/203 601/6 |
| 2012/0136280 A1* | 5/2012 | Rosenberg | A61N 1/0408 601/2 |

FOREIGN PATENT DOCUMENTS

| | | |
|---|---|---|
| WO | 03079916 A1 | 10/2003 |
| WO | 2008012827 A2 | 1/2008 |
| WO | 2010007619 A1 | 1/2010 |
| WO | 2011021184 A1 | 2/2011 |
| WO | 2012069716 | 5/2012 |

* cited by examiner

SKIN TREATMENT METHOD AND APPARATUS

This application is the U.S. National Phase application under 35 U.S.C. § 371 of International Application No. PCT/IB2013/055625, filed on Jul. 9, 2013, which claims the benefit of U.S. Provisional Application No. 61/669,187 filed on Jul. 9, 2012. These applications are hereby incorporated by reference herein.

FIELD OF THE INVENTION

The present disclosure relates to treatment of skin tissue with radiofrequency (RF) energy, e.g. for rejuvenation, and in particular to fractional RF treatment.

BACKGROUND OF THE INVENTION

Radiofrequency (RF) is a commonly used technology to heat skin tissue to treat wrinkles and skin laxity.

For skin tightening, RF is used to heat below the surface of the skin to contract collagen. Dermal collagen contracts when it is heated at temperatures between 60° C. and 70° C., and it denatures at higher temperatures, depending upon the duration of the applied heat. The shrinkage of the tissue can reach tens of percents of the heated tissue volume, and results in tightening of the skin.

A major disadvantage of the prior art for skin treatments based on uniform heating is that there is a high risk of pain and healing complications.

Fractional or pixelated treatment systems are known, which aim to provide that injured tissue is surrounded by non-injured tissue to promote healing and reduce pain, downtime and risks. US 2006/0047281 discloses an example of the use of multi-electrode RF treatment systems, where an electrode is distributed into several elements to heat discrete volumes.

Fractional devices in the prior art are not able to selectively treat small localized areas of skin without the use of complex, multiple and relatively small electrode configurations. Also, they are in general not able to non-ablatively treat skin, causing related pain and the risk of complications.

Improvements in RF treatment of skin are therefore desired.

SUMMARY OF THE INVENTION

A method of treating a skin tissue area having a skin surface according to the appended claims is provided. The method comprises the steps of: deforming the skin tissue area into a deformed shape comprising a plurality of folds in the skin tissue area; arranging radiofrequency (RF) electrodes in contact with the skin surface on opposite sides of the deformed skin tissue area; and, while maintaining the skin tissue area in said deformed shape, providing a spatially continuous radiofrequency (RF) energy flow between the radiofrequency electrodes on opposite sides of the deformed skin tissue area through the deformed skin tissue area, and releasing the skin tissue area from said deformed shape, thereby deforming said heated portion into a wave-shaped zone of heated skin tissue having a depth relative to the skin surface that varies between a minimum and a maximum value in a direction between said opposite sides.

The folds can be any type of undulation or corrugation of the skin tissue, ranging from smoothly varying ripples having a number of protrusions and depressions in between to one or more fully closed folds with skin tissue surface portions on opposite sides of the fold touching each other.

Thus, a temperature profile having an oscillating depth variation relative to the surface of the skin tissue area is provided and a pattern of surface heated zones and a pattern of deeper tissue heated zones are created in an efficient manner. The wavelike pattern of thermal zones in the skin tissue area is provided in a controllable manner using only two skin-contact electrodes. This facilitates treatment. Further, by using skin manipulation to distribute the energy between the dermis and epidermis, leaving certain tissue zones untreated, the resulting tissue injury is also distributed and the presence of untreated tissue promotes healing of injured tissue. By adjustment of the amplitude and/or "wavelength" of the skin tissue folds, the treatment depth can be adjusted, e.g. by determination and possible adjustment of height differences between adjacent relative protrusions and depressions. For increased accuracy, such determination may take further reference to the relief of the skin tissue area prior to deformation and/or un-deformed skin tissue portions adjacent the deformed skin tissue area. A suitable apparatus for performing the method may comprise a profilometer coupled with a memory for storing reference data and a controller for comparing measurement data with stored reference data.

In a particular embodiment, the skin tissue area comprises an epidermis layer and a dermis layer, and an amplitude of at least part of the folds is arranged such that at least a part of the path defined by the spatially continuous flow of radiofrequency energy between the radiofrequency electrodes and through the deformed skin tissue area extends through a portion of the dermis layer. Thus, the heating pattern extends through the epidermis and dermis that connect through the dermal-epidermal junction. When the treatment is directed also to both the dermis and the epidermal-dermal junction, then the RF treatment can also target pigmentation and induce skin textural changes through neocollagenesis. Heating the dermis can initiate such neocollagenesis and/or neoelastogenesis, heating the epidermal-dermal junction can stimulate the melanocytes and basal cell layer, and heating the epidermis can incite a healing response and also target pigmentation. As a result, skin rejuvenation and tightening may be improved.

With regard to the dermis, the main disadvantage of the known methods and devices relying on uniform dermal heating is that the heating is difficult to control. In particular for mono-polar and bipolar RF configurations, the time for heating the tissue can be in the millisecond range and the heat immediately dissipates into the surrounding tissue. Overheating can lead to patient discomfort, burns and fat atrophy. The presently provided method overcomes such disadvantage by dispersing the heat in the dermis into local treatment zones, providing slow heating of the dermis compared to known uniform heating systems, which allows for more control.

The step of providing the spatially continuous radiofrequency energy flow between the radiofrequency electrodes and through the deformed skin tissue area may comprise heating at least a portion of the deformed skin tissue area to a temperature above about 60 degrees Celsius.

Dermal collagen contracts when it is heated to temperatures between 60° C. and 70° C., and it denatures at higher temperatures, which effect can depend on the duration of the applied heat. The shrinkage of the tissue can reach tens of percents of the heated tissue volume, and results in tightening of the skin. To prevent denaturation and/or necrosis, the skin tissue area may be heated to a temperature in a range of 60-70 degrees Celsius, and heating to a higher temperature can be prevented.

The step of deforming the skin tissue area into a deformed shape comprises deforming at least a portion of the skin tissue area using a mechanical deformer. Use of a mechanical deformer, e.g. a compression device, facilitates providing and/or maintaining a desired deformed shape reliably, also over prolonged and/or repetitive application of the method. Such a method may suitably comprise pressing a mask into a portion of the skin tissue area, compressing at least two portions of skin tissue towards each other and/or applying vacuum suction to at least part of the skin tissue area, so that the skin may be deformed in different ways and according to a desired pattern. The mask suitably comprises a pattern of protrusions corresponding to the plurality of folds to be formed into the skin tissue area, and application of vacuum suction suitably comprises applying vacuum suction to one or more vacuum chambers corresponding to the plurality of folds to be formed in contact with the skin tissue area.

In an embodiment, the step of deforming the skin tissue area is performed by engaging the skin tissue with the radiofrequency electrodes, in particular by bringing the skin surface in frictional contact with the radiofrequency electrodes, and displacing the electrodes towards each other, which facilitates arrangement of the electrodes around the deformed skin tissue to be treated. In a particular embodiment, the RF electrodes may be hand-held by a person performing the treatment, e.g. with RF electrodes imbedded into the fingers of a flexible glove, allowing simultaneous skin manipulation and RF treatment.

The method may further comprise at least one of the steps of dermabrasion, microdermabrasion, the application of microlesions and outer skin layer resurfacing to promote rejuvenation of the skin tissue.

In accordance with the above, in an aspect, an apparatus for treating a skin tissue area having a skin surface is provided. The apparatus comprises a skin tissue deformer configured to form the skin tissue area into a deformed shape comprising a plurality of folds in the skin tissue area and to maintain the skin tissue area in the deformed shape, and a number of radiofrequency (RF) electrodes, configurable to be in contact with the skin surface on opposite sides of the deformed skin tissue area. The apparatus is configured for applying, while maintaining the skin tissue area in said deformed shape, a spatially continuous radiofrequency (RF) energy flow between the radiofrequency electrodes on opposite sides of the deformed skin tissue area through the deformed skin tissue area, and for releasing the skin tissue area from said deformed shape after application of the spatially continuous radiofrequency energy flow. Thereby, a portion of the deformed skin tissue area is heated such that, when the skin tissue area is released from said deformed shape, said heated portion is deformed into a zone of heated skin tissue having a depth variation relative to the skin surface that varies between a minimum and a different maximum value in a direction between said opposite sides. Thus, application of fractional RF treatment is facilitated.

In a particular embodiment, the apparatus comprises a control unit configured and arranged to operate the apparatus so as to form the skin tissue area into a deformed shape comprising a plurality of folds in the skin tissue area, maintain the skin tissue area in the deformed shape by application of the skin tissue deformer, and apply a spatially continuous radiofrequency (RF) energy flow through the deformed skin tissue area by application of the radiofrequency electrodes when arranged on opposite sides of the deformed skin tissue area, and release the skin tissue area from said deformed shape by application of the skin tissue deformer after application of the spatially continuous radiofrequency energy flow.

In a particular embodiment, the apparatus is configured to heat at least a portion of the deformed skin tissue area to a temperature above about 60 degrees Celsius to cause contraction and/or denaturation of collagen for tightening of the skin tissue and/or inciting rejuvenation. Preferably, the heating is performed to a temperature in a range of about 60-70 degrees Celsius.

The apparatus may comprise a controller configured to operate the apparatus as a function of one or more input signals, e.g. from a user interface. In an embodiment, the controller may be configured to operate the deformer.

The apparatus may comprise a thermometer configured to detect a temperature of the skin tissue area and the controller may be configured to operate the apparatus as a function of one or more signals from the thermometer. This facilitates controlled operation, e.g. providing safety against overheating and/or including a feedback mechanism. The apparatus may also include detection of impedance of the skin to give feedback, for example, on the temperature or the extent of heating.

In order to provide a controlled thermal pattern, the skin tissue deformer may comprise a mask comprising a pattern of protrusions corresponding to the plurality of folds to be formed into the skin tissue area to define a plurality of adjacent skin tissue folds. Alternatively, the skin tissue deformer may comprise a vacuum system comprising one or more vacuum chambers corresponding to the plurality of folds to be formed for creation of skin tissue folds by vacuum suction. The skin tissue deformer may be configured to provide a two-dimensional array of skin tissue folds. The spacing of the mask and/or the vacuum pressure may assist in determining the depth of the skin tissue folds.

The skin tissue deformer may comprise a plurality of probes and/or radiofrequency electrodes configured to be brought into frictional contact with the skin surface and engage the skin surface, and to be movable with respect to each other to thereby deform the skin tissue area into the deformed shape. The probes and/or electrodes may comprise surface portions providing a high coefficient of friction when in contact with human skin surface, e.g. comprising a rubber and/or roughened contact surface for contacting human skin, and/or comprising one or more vacuum cups configured to engage the skin by suction. Thus, skin tissue may be pushed and/or pulled in a desired direction to fold the skin tissue area. Such a deformer facilitates maintaining a particular deformation for extended periods of time non-invasively. The deformer may be adjustable to establish and/or maintain a particular deformed shape. In an embodiment, the apparatus may comprise a flexible glove comprising the RF electrodes.

Preferably, the apparatus comprises a cooler, e.g. being configured to cool the skin tissue area to a temperature at or near normal body temperature. Thus, a particular thermal gradient in the skin may be provided and/or a hot feeling may be soothed.

The cooler may comprise a heat sink, such as a radiator with a high thermal conductance and a large surface, convective cooling or chilled gas, possibly in combination with a heat sink, and/or a cryogenic cooling element, but preferred is an active cooling element such as a Peltier-element and/or a refrigerator device, which may be controllably operated.

The apparatus may comprise a profilometer, e.g. to provide information on a height profile of a skin tissue relief feature. The profilometer may be configured to provide one or more signals, such as visual indications and/or signals to be used as input signals, to a controller configured to operate the apparatus as a function of one or more signals from the profilometer, e.g. for adjustment of the deformer to provide a deformation of a desired amplitude and/or wavelength. The profilometer can also provide information on the progress and/or effectiveness of the method. It is conceivable that a plurality of cycles of heating, cooling, reheating and re-cooling are performed according to the method presented herein until a particular skin tissue profile is reached.

The profilometer may comprise a mechanical detector, e.g. with one or more mechanical probes, an electrical detector, e.g. with one or more capacitive or resistive sensors and/or an optical detector, e.g. with an optical reflectance sensor, a camera etc. The profilometer may be coupled with a memory and/or a controller, which may be contained in the apparatus.

The apparatus may be configured for performing dermabrasion, microdermabrasion, and for the application of microlesions and/or outer skin layer resurfacing to the skin tissue area, for which purpose the apparatus comprises, e.g., a mechanical skin tissue perforator, a suitable light source, an ultrasound generator etc. Such apparatus facilitates inducing skin rejuvenation in addition to providing a reformed skin shape to provide a smoother, younger-looking skin.

The apparatus may comprise a controller, possibly having a memory which may be programmable, the controller being configured to operate the apparatus as a function of one or more signals from a thermometer, a profilometer and/or a user interface.

DETAILED DESCRIPTION OF EMBODIMENTS

It is noted that, in the drawings, like features may be identified with like reference signs. It is further noted that the drawings are schematic, not necessarily to scale and that details that are not required for understanding the present invention may have been omitted. The terms "upward", "downward", "below", "above", and the like relate to the embodiments as oriented in the drawings. Further, elements that are at least substantially identical or that perform an at least substantially identical function are denoted by the same numeral.

Figure 1:
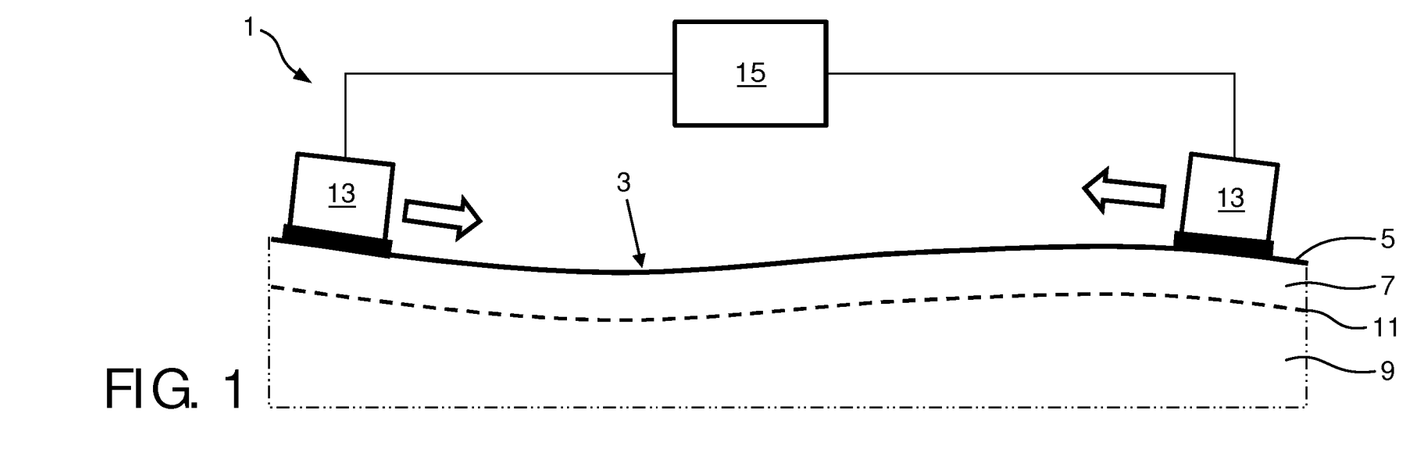
FIGS. 1-4 show steps of a method of treating a skin tissue area.
Figure 2:
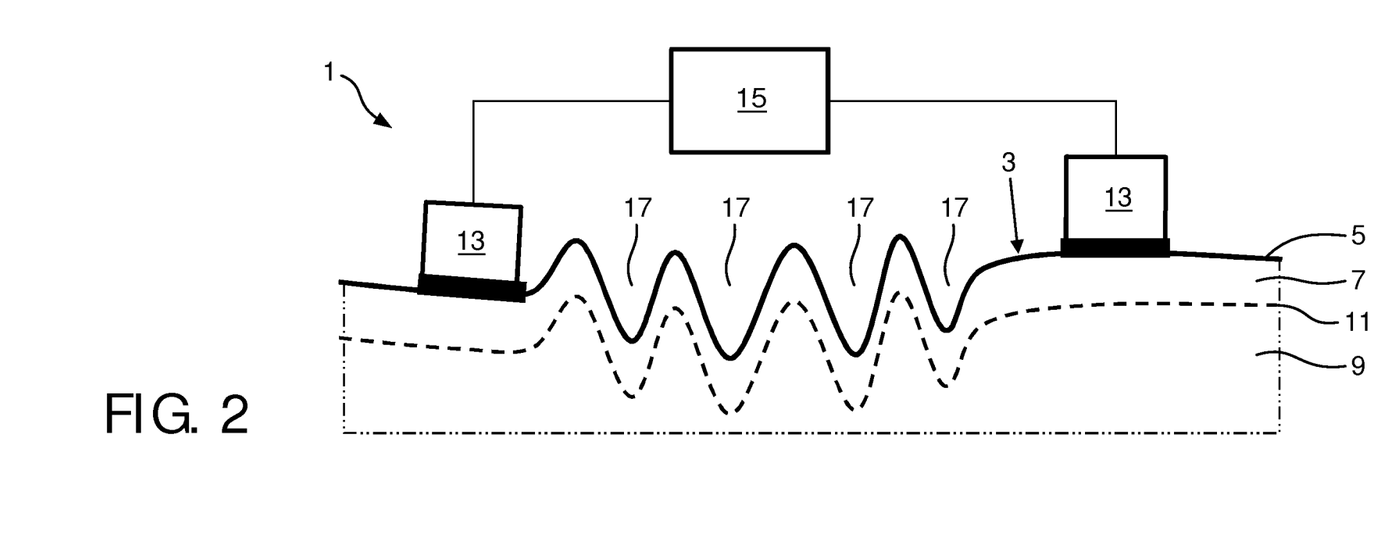

FIGS. 1 and 2 show steps of the method of treating a skin tissue area. FIGS. 1 and 2 show in cross section an apparatus 1 for treating skin tissue, which apparatus is placed on a human skin tissue area 3. The skin tissue area 3 has a skin surface 5, an epidermis layer 7, a dermis layer 9 and a dermal-epidermal junction 11. Below the dermis layer 9 further tissue layers are present, which are not shown. The apparatus 1 comprises a number of radiofrequency (RF) electrodes 13, arrangeable in contact with the skin surface 5, and a power source 15 connected with the RF electrodes 13 to apply RF energy to the skin tissue area 3.

In this embodiment, the RF electrodes 13 are configured to be brought into frictional contact with the skin surface 5, and to be movable with respect to each other (indicated with the arrows in FIG. 1) to thereby deform the skin tissue area 3 between the electrodes 13 from an initial shape (FIG. 1) into a deformed shape (FIG. 2) having a plurality of folds 17 in the skin tissue area 3 with relative protrusions and depressions of a desired amplitude and distance relative to each other, so that the dermal-epidermal junction 11 is folded into an oscillating wavy shape (FIG. 2).

Figure 3:
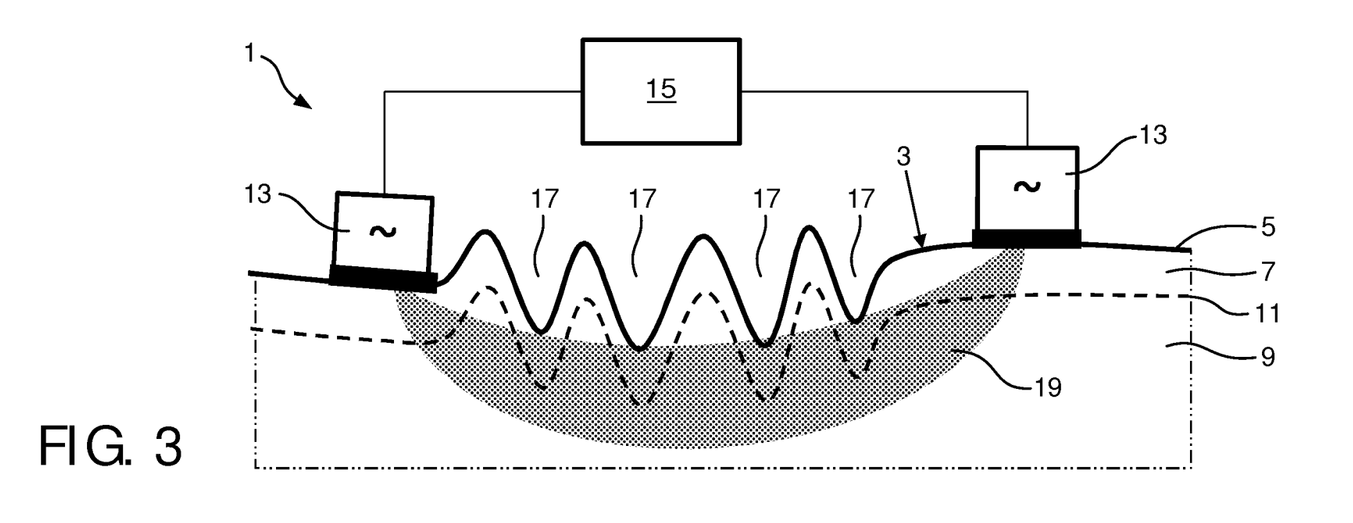

FIG. 3 indicates operation of the RF source 15, with the RF electrodes 13 in bipolar configuration and the polarity of the electrodes being varied with respect to each other, at high radiofrequency, while maintaining the skin tissue area 3 in the deformed shape. The RF energy flow will take the path of least electrical resistance between the RF electrodes 13 which generally corresponds to the shortest geometrical path. Thus, a spatially continuous radiofrequency energy flow is provided from one RF electrode 13 to the RF electrode 13 on the opposite side of the deformed skin tissue area 3 through the deformed skin tissue area 3, wherein the RF energy is distributed in a skin tissue zone 19 extending at varying depths with respect to the skin surface 5, here also crossing the dermal-epidermal junction 11. The RF energy is dissipated in the skin tissue zone 19 and heats it. The temperature and spatial extent of the skin tissue zone 19 are related to the power and duration of the applied RF energy.

Figure 4:
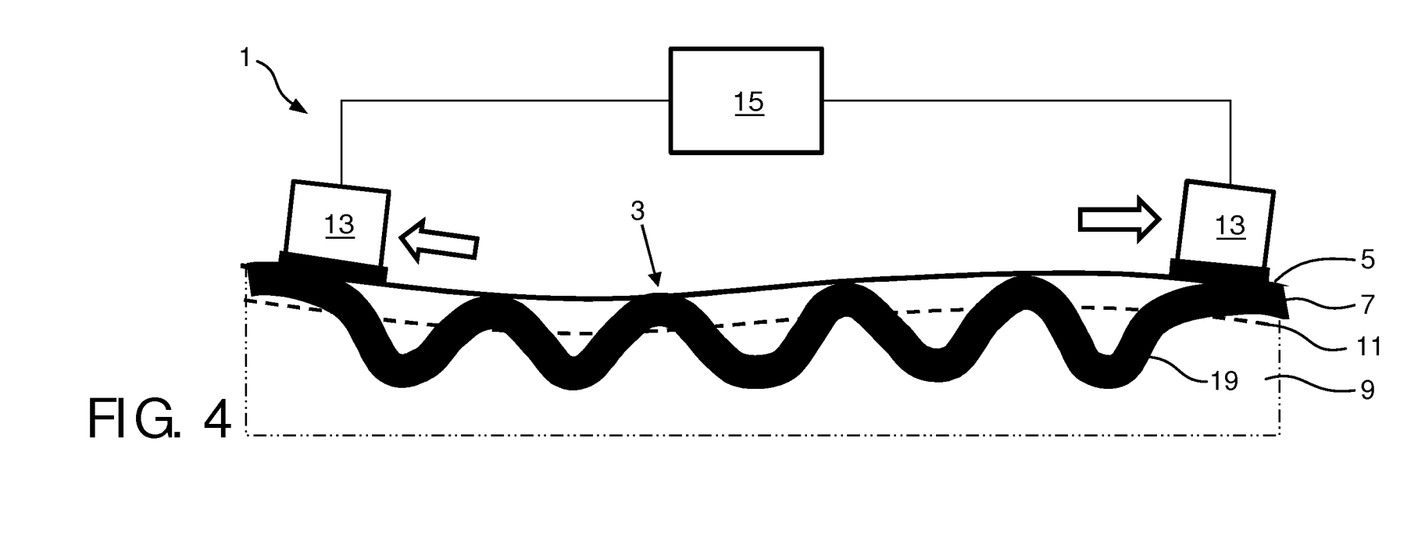

FIG. 4 shows that, if (the pinching force on) the skin tissue 3 is released and the folds 17 are removed, the skin tissue zone 19 that has been heated by the RF energy retains its depth variation relative to the skin surface and the skin tissue zone 19 is accordingly deformed into a wave-shaped zone having a depth that varies between a minimum and a different maximum value relative to the skin surface in a direction between said opposite sides. The depth profile of the heated skin tissue may be suitably determined with respect to (a maximum of) the temperature profile perpendicular to the skin surface and/or with respect to one or more isotherms in the skin tissue. The minimum depth value may be substantially zero and the maximum depth value may be several millimeters or even over a centimeter for deep skin folds 17, e.g. on a person's belly- or back region.

Figure 5:
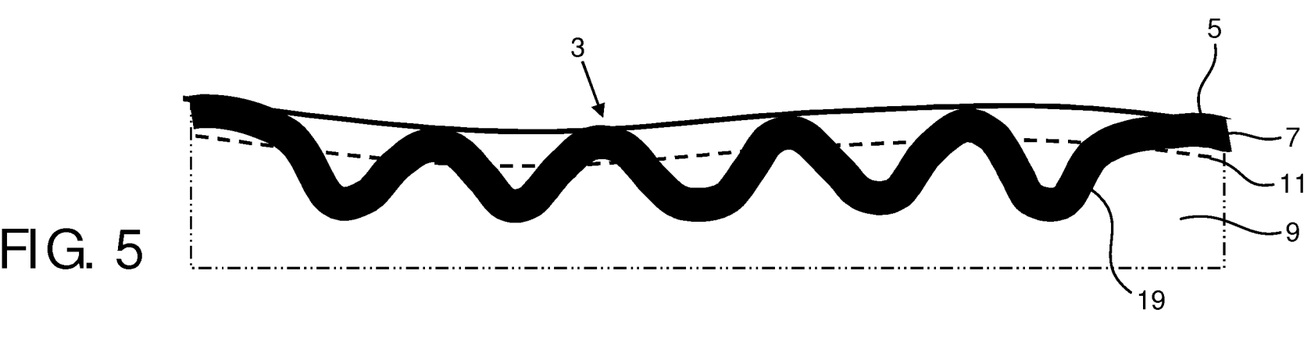
FIG. 5 is a cross sectional view of skin tissue treated with the method.
Figure 6:
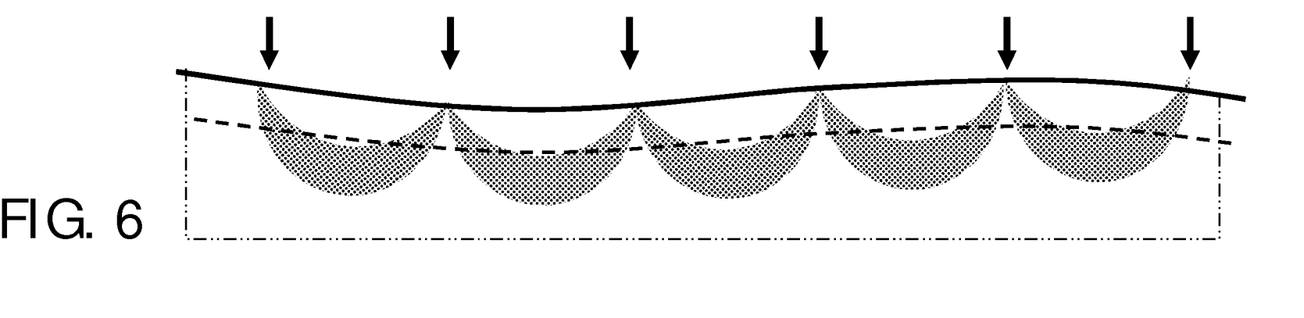
FIG. 6 indicates skin tissue treated with fractional RF treatment, for comparison.

FIG. 5 shows the skin tissue area 3 of FIG. 4 without the apparatus 1. FIG. 6 indicates an RF energy distribution, and thus the associated heating pattern, envisioned when using a known fractional RF apparatus with a relatively dense electrode pattern indicated by means of the bold arrows. The similarity will be striking to the skilled reader. However, as set out above, the RF fields between each pair of adjacent electrodes extend generally to little depth, which depth cannot be accurately controlled. Further, fractional RF systems and the use thereof are significantly more complex and delicate as compared to the present apparatus and method.

Figure 7:
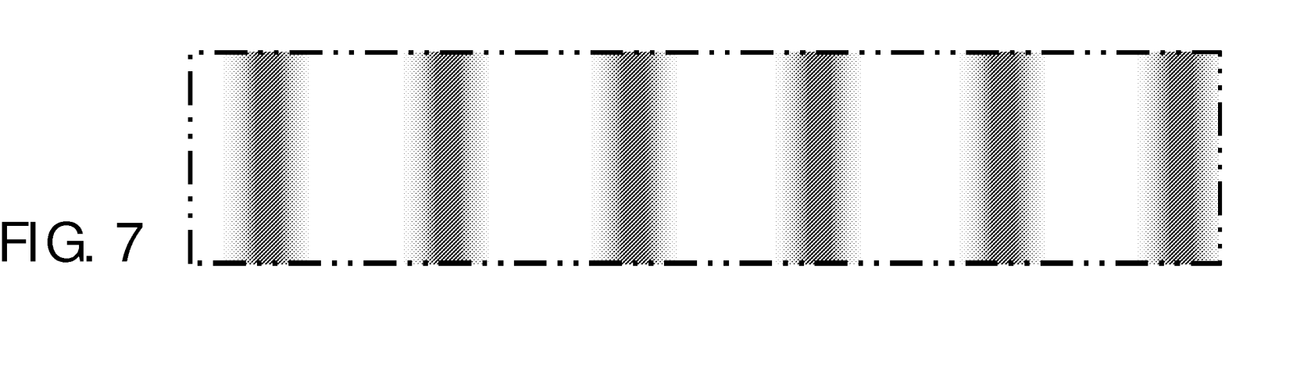
FIG. 7 is a top view of skin tissue treated with the method.

FIG. 7 is a schematic top view of the skin surface 5 of a skin tissue area 3 treated with an embodiment of the presently provided method, indicating a striped pattern of heated (dark) versus cooler (light) skin tissue portions, corresponding to superficial and deep portions of the heated skin tissue zone 19, respectively. The temperature of the relatively superficial portions, corresponding to the bottoms of the folds 17, is indicative of the temperature in the deeper regions corresponding to the maxima of the folds 17.

Figure 8:
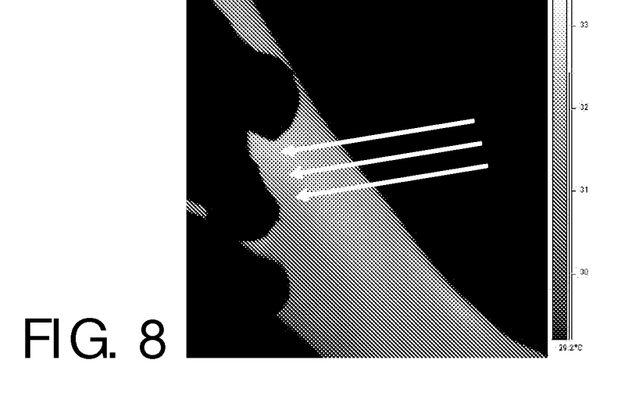
FIGS. 8-12 are thermographs of steps of a method of treating a skin tissue area, a corresponding cartoon and a graph of a measurement result, respectively.
Figure 9:
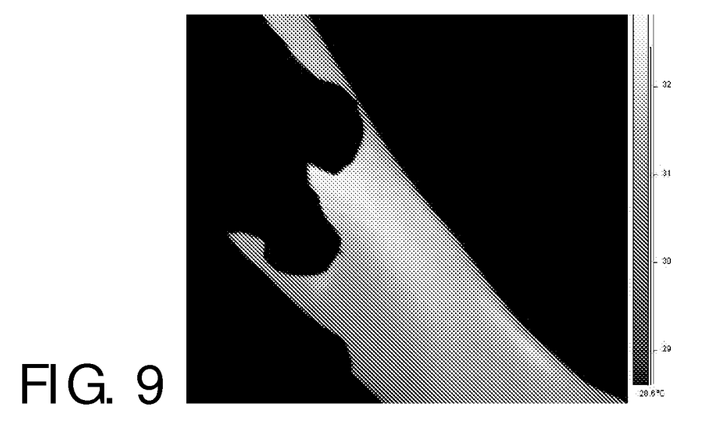
Figure 10:
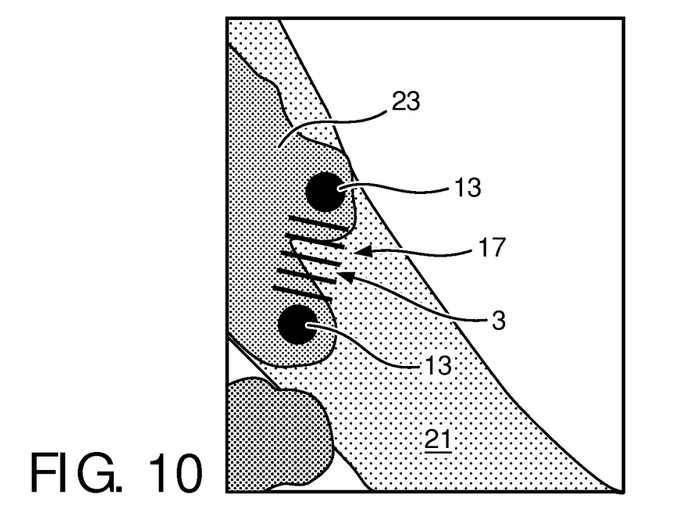
Figure 11:
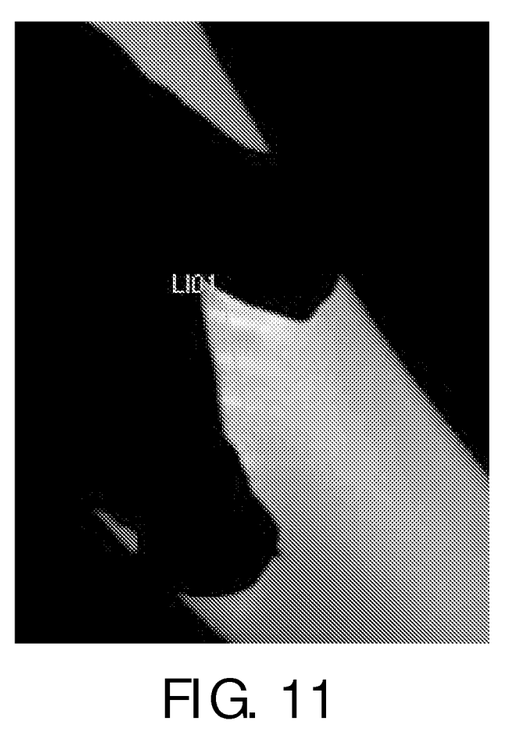

FIGS. 8, 9 and 11 show photographs, taken with a temperature-sensitive camera, of an underarm of a test subject. FIG. 10 is a cartoon of FIGS. 8 and 9. The thermal images were recorded with an FLIR infrared camera adjusted for the emissivity of human skin (0.98). For this experimental system, bipolar RF electrodes were embedded into fingers of a flexible glove, allowing simultaneous skin manipulation and RF treatment. FIG. 10 shows the underarm 21, the positions of the fingers 23 and the associated electrodes 13, as well as the folds 17 in the treated skin tissue area 3.

Figure 12:
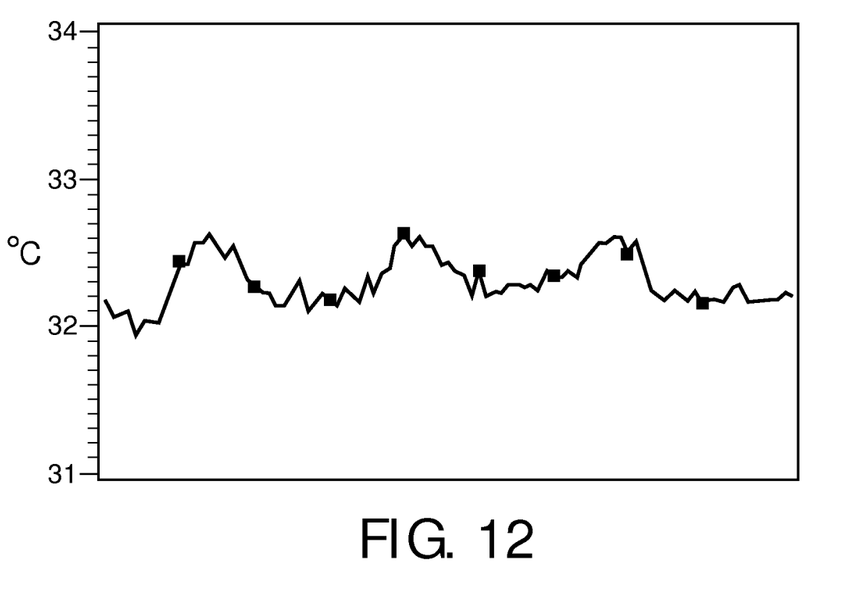

FIG. 8 shows skin tissue being pinched between (the fingers 22 carrying) the RF electrodes, with individual folds 17 indicated with arrows, see also FIG. 10. The color scale corresponds to a surface temperature range of about 29.2-33.5° C. FIG. 9 shows the effect of RF being applied to the pinched area of FIG. 8 for 2.0 seconds, increasing the average surface temperature between the electrodes to 33° C. from about 31° C. FIG. 11 shows the effect of the heating when the pinching pressure is released. Generally linear and parallel portions with elevated surface temperatures of about 32.7° C. have been created in between the electrodes. FIG. 12 shows a line profile analysis through the heated zone as indicated in FIG. 11, showing the periodic surface temperature pattern created by the RF energy, comparable to FIG. 7. This allows controlling the operation of the apparatus by employing a suitable thermometer and a controller.

Figure 13:
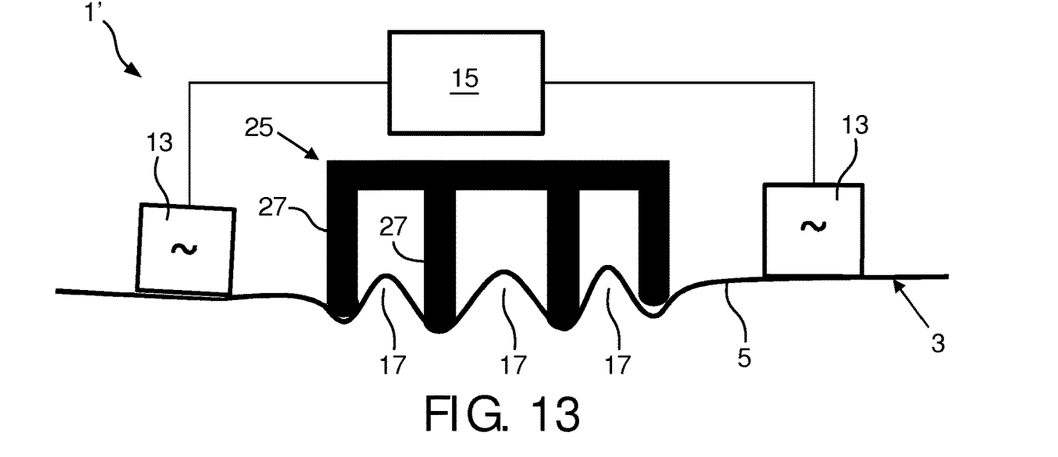
FIG. 13 indicates an embodiment of an apparatus for treating a skin tissue area as disclosed herein.

FIG. 13 shows, similar to FIGS. 1-4, an embodiment of an apparatus 1' that is particularly suitable for skin tissue areas 3 that are not easily folded by pinching as explained supra, comprising a mechanical deformer 25 in the form of a mask comprising a pattern of electrically insulating protrusions 27 corresponding to the plurality of folds 17 to be formed into the skin tissue area 3.

Figure 14A:
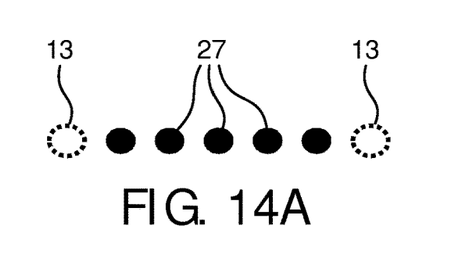
FIGS. 14A-14F indicate mask patterns for use in embodiments of an apparatus.
Figure 14B:
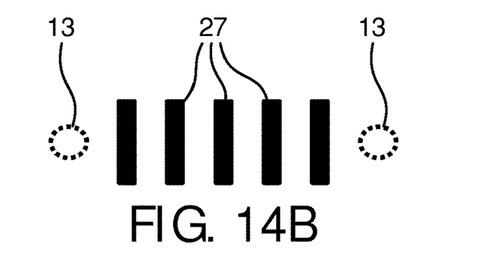
Figure 14C:
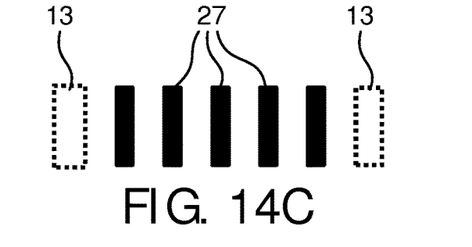
Figure 14D:
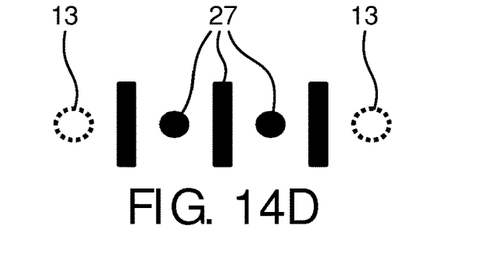
Figure 14E:
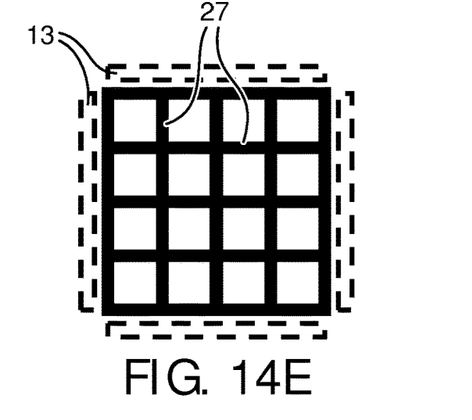
Figure 14F:
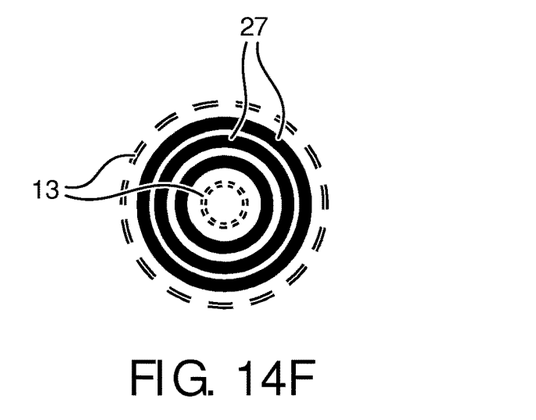

Top views of typical patterns of electrodes 13 and protrusions 27 for forming a one-dimensional array of depressions and folds into the skin tissue area 3 to be treated are shown in FIGS. 14A-14D, and FIGS. 14E-14F similarly show exemplary patterns of protrusions 27 configured to deform the skin tissue area 3 into a deformed shape comprising a two-dimensional array of skin tissue folds 17. The deformer can have pins or edges of any type and/or configuration, e.g. as indicated in FIG. 14A, pins 27 placed in line with RF electrodes 13 and/or elongated edges placed in line with electrodes 13 as in FIGS. 14B-14C. The electrodes 13 can have different geometries and can even have a high aspect ratio to cover a significant area of skin. Other patterns, possibly irregularly shaped and/or producing non-equidistant or unevenly deep skin tissue folds, are equally conceivable.

Figure 15A:
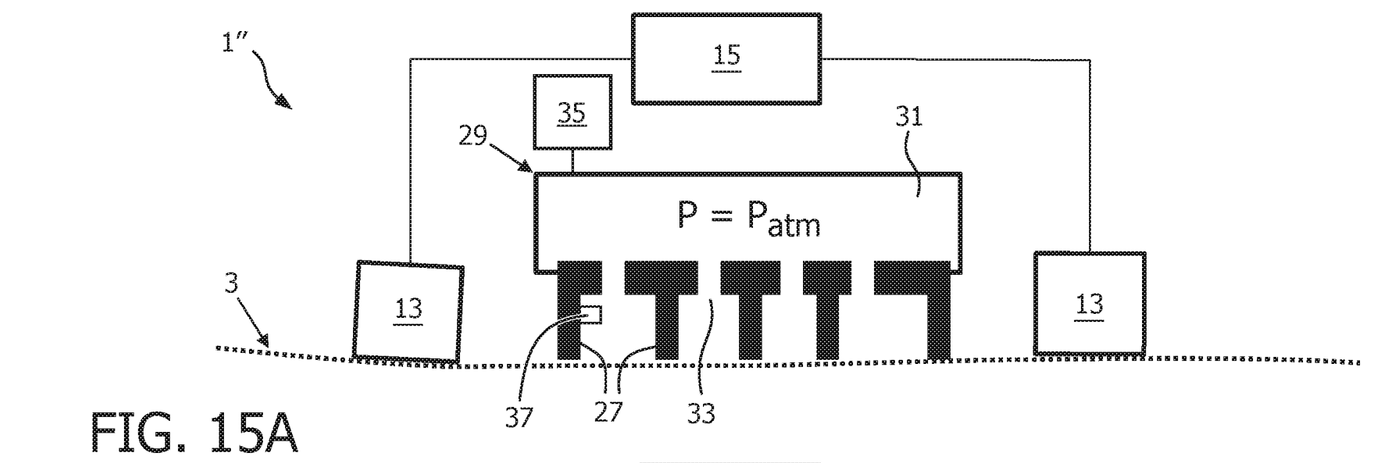
FIGS. 15A-15B indicate another embodiment of an apparatus for treating a skin tissue area as disclosed herein.
Figure 15B:
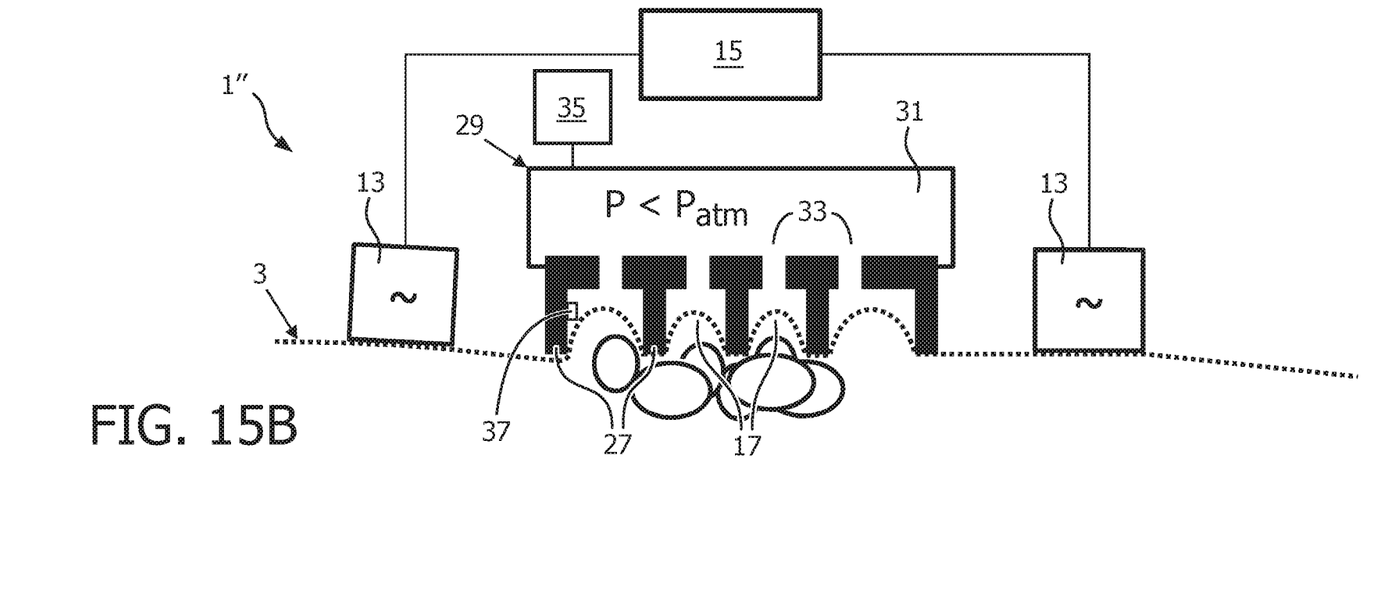

FIGS. 15A-15B show, similar to FIGS. 1-4 and 13, a further embodiment of an apparatus 1" comprising a mechanical deformer 29 comprising a plurality of electrically insulating protrusions 27 connected with a vacuum system 31 capable of providing a sub-atmospheric pressure between at least some of the protrusions 27. When the deformer 29 is placed in contact with the skin surface 3 and the vacuum system is activated, the skin 3 can be sucked into the areas 33 of negative pressure between the protrusions 27 and conform to the edges 27 forming the desired folds 17 (FIG. 15B). The vacuum pressure may be controlled by employing a suitable profilometer 35 and a controller 37.

Figure 16A:
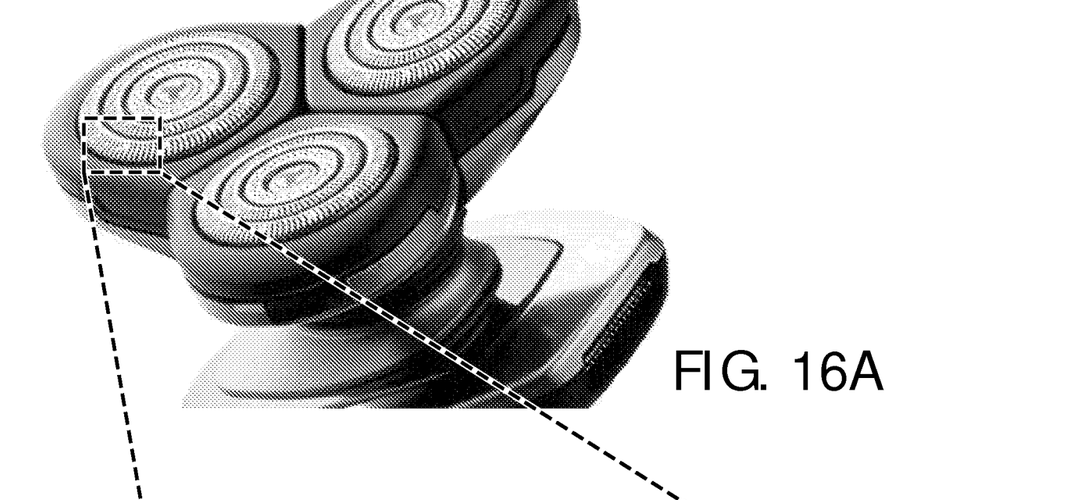
FIGS. 16A-16B indicate part of an embodiment of an apparatus with a combination mask and electrode arrangement.
Figure 16B:
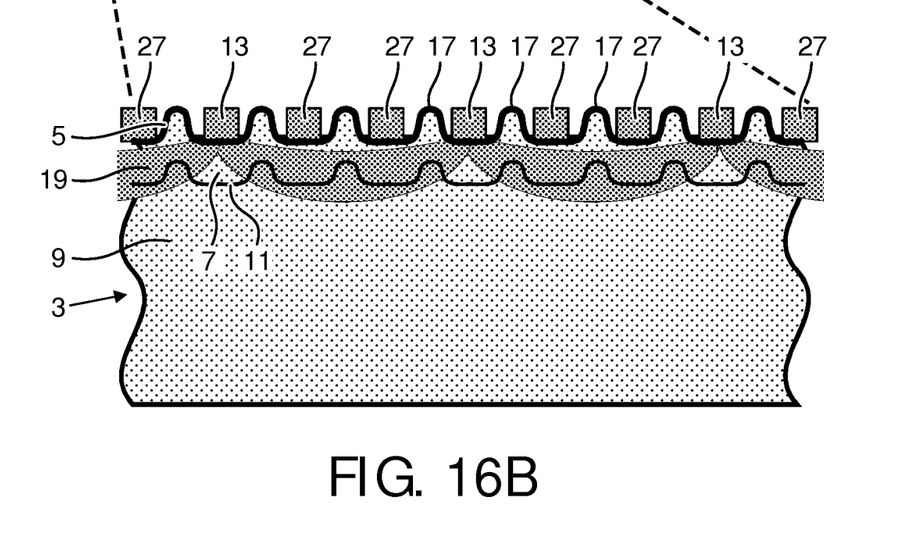

In a preferred embodiment, the insulating deformer portions 27 and RF electrodes 13 are integrated into a single series of objects, forming folds 17 by doming of the skin 3 between the objects when they are pressed against the skin surface 5. Such an arrangement is shown in the embodiment of FIG. 16A, the use of which is shown in FIG. 16B in similar fashion as in FIGS. 1-4, 13 and 15A-15B. The shown embodiment, resembling a known shaving device, enables the production of a radial pattern of skin folds 17 and associated heated skin tissue zones 19.

In particular for flexible skin portions, e.g. facial skin, deforming features 27 of a skin deformer may be closely spaced in the millimeter or even sub-millimeter range, and fold amplitudes in the range of about 100-300 micrometer, e.g. in a range of about 150-250 micrometer, may suffice for suitable heating of the dermal-epidermal junction which may be located at a depth of about 100-200 micrometer from the skin surface. Little separation between the RF electrodes 13 may reduce the RF power required for suitable skin tissue heating.

The presently provided apparatus allows treating much smaller zones of tissue layers than known devices, which serve to treat skin tissue areas of 1-50 $cm^2$, typically regions of about 10 $cm^2$. However, the use of the present apparatus and method is not dictated by inter-electrode distances and much smaller treatment areas and/or details are possible. For example, folded tissue areas with an interdistance of 0.1-2 cm (with respect to a direction generally perpendicular to the folds) and electrode sizes of 0.1-1 cm are possible, resulting in heated tissue zones with typical sizes and/or details of the order of 0.01-2 $cm^2$. Also, in apparatus using vacuum pressure a relatively small under-pressure may suffice, e.g. 0.01-0.05 atmosphere (negative pressure) with respect to ambient pressure. Other variations to the disclosed embodiments can be understood and effected by those skilled in the art in practicing the claimed invention, from a study of the drawings, the disclosure, and the appended claims. For instance, any template capable of forming at least two skin protrusions can be used with both positive and negative pressure vacuum configurations. The fold depth and interfold distance can be varied to influence the treatment.

The deformer or the vacuum surface can be used to conductively cool the skin to enhance the RF heating in deeper tissue layers.

An additional feature of the skin manipulation can be a profilometer, e.g. a contact sensor and/or an optical sensor that facilitate determination of whether the amplitude of at least a portion of the skin tissue folds, e.g. particular skin tissue protrusions between deformer structures, are sufficient to trigger application of RF current.

Any type of RF power settings can be used. In one embodiment, a frequency of 1 MHz and a power of 25 W is applied to the skin for a sustained period in the range of 1 msec-5 sec.

In any one of the embodiments of an apparatus 1, 1', 1" according to the invention described before, the apparatus may comprise a control unit configured and arranged to operate the apparatus so as to form the skin tissue area into the desired deformed shape comprising a plurality of folds in the skin tissue area, maintain the skin tissue area in the deformed shape by application of the skin tissue deformer, and apply the desired spatially continuous radiofrequency energy flow through the deformed skin tissue area by application of the radiofrequency electrodes when arranged on opposite sides of the deformed skin tissue area, and release the skin tissue area from said deformed shape by application of the skin tissue deformer after application of the spatially continuous radiofrequency energy flow.

It is further noted that in the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different embodiments and/or dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating an apparatus for treating a skin tissue area having a skin surface, comprising steps of:
    deforming the skin tissue area comprising an epidermis layer and a dermis layer, by a skin deformer, into a deformed shape comprising a plurality of folds in the skin tissue area with relative protrusions and depressions of a desired amplitude and distance relative to each other such that a dermal-epidermal junction is folded into an oscillating wavelike shape, comprising
    (i) applying vacuum suction sourced from a vacuum system supplying a vacuum pressure to one or more vacuum chambers corresponding to the plurality of skin tissue folds to be formed in contact with the skin tissue area, and
    (ii) controlling the vacuum pressure by a profilometer and a control unit configured to operate the profilometer, wherein said vacuum pressure is a negative vacuum pressure between 0.01-0.05 atmosphere with respect to ambient pressure;
    arranging at least two radiofrequency electrodes in bipolar configuration, brought into frictional contact with the skin surface on opposite sides of the deformed skin tissue area, the at least two radiofrequency electrodes comprising surface portions providing a high coefficient of friction when in contact with said skin surface; and
    providing a spatially continuous radiofrequency energy flow between the at least two radiofrequency electrodes on opposite sides of the deformed skin tissue area through the deformed skin tissue area while maintaining the skin tissue area in said deformed shape, wherein the RF energy is distributed in a skin tissue zone extending at varying depths with respect to the skin surface while also crossing the dermal-epidermal junction, and wherein the RF energy is dissipated in the skin tissue zone and heats it,
    adjusting a treatment depth of skin tissue folds formed in the deformed skin tissue area, by the profilometer, by adjusting height differences between relative protrusions and depressions in said skin tissue folds, wherein said height difference adjustments are determined from information provided by the profilometer on a height profile of a skin tissue relief feature,
    releasing the skin tissue area from said deformed shape, thereby deforming a heated portion into a wave-shaped zone of heated skin tissue having a depth relative to the skin surface that varies between a minimum and a maximum value in a direction between said opposite sides and crosses the dermal-epidermal junction,
    wherein the deformed skin tissue area has an interdistance of 0.1 to 2 cm with respect to a direction generally perpendicular to the folds,
    wherein a temperature and a spatial extent of the waveshaped zone is related to a power and a duration of the applied RF energy, and
    wherein the minimum depth value is substantially zero and the maximum depth value may be in a range of several millimeters to a centimeter or more, thus facilitating a fractional RF treatment, and
    detecting a temperature profile of the zone of heated skin tissue,
    determining a depth profile of the zone of heated skin tissue with respect to a maximum of the temperature profile perpendicular to the skin surface or with respect to one or more isotherms in the skin tissue, and
    conductively cooling the skin tissue area to a temperature at or near normal body temperature to provide a particular thermal gradient in the skin tissue area, wherein the conductive cooling is controllably operated.

2. The method of claim 1, wherein an amplitude of at least part of the folds is such that at least a part of the spatially continuous flow of the radiofrequency energy between the at least two radiofrequency electrodes and through the deformed skin tissue area extends through a portion of the dermis layer.

3. The method of claim 2, wherein said amplitude of at least part of the folds is in a range of 100-200 micrometer.

4. The method of claim 1, wherein the step of providing the spatially continuous radiofrequency energy flow between the at least two radiofrequency electrodes and through the deformed skin tissue area comprises heating at least a portion of the deformed skin tissue area to a temperature above 60 degrees Celsius.

5. The method of claim 1, wherein the step of deforming the skin tissue area into said deformed shape comprises deforming at least a portion of the skin tissue area using a mechanical skin deformer.

6. The method of claim 5, wherein the step of deforming the skin tissue area is performed by bringing the skin surface into frictional contact with the at least two radiofrequency electrodes, and displacing the at least two radiofrequency electrodes towards each other.

7. The method of claim 1, wherein the vacuum system is capable of providing a sub-atmospheric pressure between at least some of the protrusions.

8. The method of claim 1, wherein the step of arranging the at least two radiofrequency electrodes in contact with the skin surface on opposite sides of the deformed skin tissue area is performed by embedding bipolar radiofrequency electrodes into fingers of a flexible glove allowing simultaneous skin manipulation and radiofrequency treatment.

9. The method of claim 1, wherein skin deforming features resulting from an application of the skin deformer are closely spaced skin deforming features in one of a millimeter range and a sub-millimeter range.

10. The method of claim 1, wherein said at least two radiofrequency electrodes comprise a rubber and/or roughened contact surface for contacting said skin tissue area.

11. The method of claim 1, wherein said at least two radiofrequency electrodes comprise one or more vacuum cups configured to engages said skin tissue area by suction.

12. An apparatus for treating a skin tissue area having a skin surface, comprising:

a skin tissue deformer configured to form the skin tissue area comprising an epidermis layer and a dermis layer into a deformed shape comprising a plurality of folds in the skin tissue area with relative protrusions and depressions of a desired amplitude and distance relative to each other such that a dermal-epidermal junction is folded into an oscillating wavelike shape, and to maintain the skin tissue area in the deformed shape, and at least two radiofrequency electrodes, configurably arranged in a bipolar configuration to be brought into frictional contact with the skin surface on opposite sides of the deformed skin tissue area, said at least two radiofrequency electrodes being movable with respect to each other, said at least two radiofrequency electrodes comprising surface portions providing a high coefficient of friction when in contact with said skin surface, and a vacuum system comprising one or more vacuum chambers corresponding to the plurality of folds to be formed for creation of skin tissue folds by vacuum suction, a thermometer configured to detect a temperature of the skin tissue area, a controller having an associated programmable memory, the controller being configured to:

operate the apparatus as a function of one or more signals from the thermometer, a profilometer and a user interface, the profilometer configured to:
   provide information on a height profile of a skin tissue relief feature,
   provide one or more signals as input to the controller configured to operate the apparatus as a function of said one or more signals to thereby adjust the vacuum system,
   adjust a treatment depth of skin tissue folds formed in the deformed skin tissue area by adjusting height differences between relative protrusions and depressions in said skin tissue folds, wherein said height difference adjustments are determined from said provided information provided on said height profile of said skin tissue relief feature, a cooler configured to cool the skin tissue area to a temperature at or near normal body temperature to provide a particular thermal gradient in the skin tissue area, wherein the apparatus is configured for applying, while maintaining the skin tissue area in said deformed shape, a spatially continuous radiofrequency energy flow between the at least two radiofrequency electrodes on opposite sides of the deformed skin tissue area through the deformed skin tissue area, and for releasing the skin tissue area from said deformed shape after application of the spatially continuous radiofrequency energy flow, and wherein the apparatus is configured to release the skin tissue area from said deformed shape, thereby deforming a heated portion into an oscillatory wave-shaped skin tissue zone of heated skin tissue extending at various depths within the skin tissue, wherein a depth variation relative to the skin surface that varies between a minimum and a maximum depth value in a direction between said opposite sides, and crosses the dermal-epidermal junction, wherein the temperature and spatial extent of the skin tissue zone is related to a power and a duration of the applied RF energy, wherein the minimum depth value is substantially zero and the maximum depth value may be in a range of several millimeters to a centimeter or more, thus facilitating a fractional RF treatment, and a vacuum system configured to apply vacuum suction sourced from vacuum pressure supplied by said vacuum system, to deform the skin tissue area into the deformed shape, wherein said vacuum pressure is controlled by the profilometer and the controller configured to operate the profilometer, and wherein the deformed skin tissue area has an interdistance of 0.1 to 2 cm with respect to a direction generally perpendicular to the folds.

13. The apparatus of claim 12, wherein said control unit is further configured and arranged to:
   operate the apparatus so as to form the skin tissue area into the deformed shape comprising a plurality of folds in the skin tissue area,
   maintain the skin tissue area in the deformed shape by application of the skin tissue deformer, and
   apply the spatially continuous radiofrequency energy flow through the deformed skin tissue area by application of the at least two radiofrequency electrodes when arranged on opposite sides of the deformed skin tissue area, and
   release the skin tissue area from said deformed shape by application of the skin tissue deformer after application of the spatially continuous radiofrequency energy flow.

14. The apparatus of claim 12, being configured to heat at least a portion of the deformed skin tissue area to a temperature above 60 degrees Celsius.

15. The apparatus of claim 12, wherein the skin tissue deformer comprises a mask comprising a pattern of protrusions corresponding to the plurality of folds to be formed into the skin tissue area.

16. The apparatus of claim 12, wherein the skin tissue deformer is configured to deform the skin tissue area into the deformed shape comprising a two-dimensional array of skin tissue folds.

17. The apparatus according to claim 12, being configured for performing dermabrasion, microdermabrasion, and for an application of microlesions and/or outer skin layer resurfacing to the skin tissue area.

18. The apparatus of claim 12, wherein the vacuum system is capable of providing a sub-atmospheric pressure between at least some of the protrusions.

19. The apparatus of claim 12, wherein the at least two radiofrequency electrodes are arranged to be in contact with the skin surface on opposite sides of the deformed skin tissue area is performed by embedding bipolar radiofrequency electrodes into fingers of a flexible glove allowing simultaneous skin manipulation and radiofrequency treatment.

20. The apparatus of claim 12, wherein skin deforming features resulting from an application of the skin deformer are closely spaced skin deforming features in one of a millimeter range and a sub-millimeter range.

21. The apparatus of claim 12, wherein said amplitude of at least part of the folds is in a range of 100-200 micrometer.

22. A method of operating an apparatus for treating a skin tissue area having a skin surface, comprising steps of:
   deforming the skin tissue area, by a skin deformer, into a deformed shape comprising a plurality of folds in the skin tissue area, wherein deforming the skin tissue area into the deformed shape comprises pressing a mask comprising a pattern of electrically insulated protrusions corresponding to the plurality of folds to be formed into the skin tissue area;

arranging at least two radiofrequency electrodes in contact with the skin surface on opposite sides of the deformed skin tissue area; and providing a spatially continuous radiofrequency energy flow between the at least two radiofrequency electrodes on opposite sides of the deformed skin tissue area through the deformed skin tissue area, thereby heating at least a portion of the deformed skin tissue area while maintaining the skin tissue area in said deformed shape; and detecting a temperature of the skin tissue area, operating the apparatus as a function of one or more control signals from said detected temperature measurement, adjusting a treatment depth of skin tissue folds formed in the deformed skin tissue area by profilometer by adjusting height differences between relative protrusions and depressions in said skin tissue folds, wherein said height difference adjustments are determined from information provided by the profilometer on a height profile of a skin tissue relief feature, and releasing the skin tissue area from said deformed shape, thereby deforming a heated portion into an oscillatory wave-shaped skin tissue zone of heated skin tissue extending at various depths within the skin tissue, wherein a depth variation relative to the skin surface that varies between a minimum depth value and a maximum depth value in a direction between said opposite sides, and crosses a dermal junction, wherein the temperature and spatial extent of the skin tissue zone is related to a power and a duration of the applied RF energy, wherein the minimum depth value is substantially zero and the maximum depth value may be in a range of several millimeters, thus facilitating a fractional RF treatment, and wherein the deformed skin tissue area has an interdistance of 0.1 to 2 cm with respect to a direction generally perpendicular to the folds.

23. The method of claim 22, wherein said at least two radiofrequency electrodes comprise a rubber and/or roughened contact surface for contacting said skin tissue area.

24. The method of claim 22, wherein said at least two radiofrequency electrodes comprise one or more vacuum cups configured to engages said skin tissue area by suction.

25. An apparatus for treating a skin tissue area having a skin surface, comprising:

a mechanical skin tissue deformer configured to deform the skin tissue area into a deformed shape to provide and maintain a desired deformed shape over prolonged and/or repetitive applications, the mechanical skin tissue deformer comprising a mask comprising a pattern of electrically insulating protrusions corresponding to a plurality of folds to be formed in the skin tissue area, at least two radiofrequency electrodes, configurably arranged to be brought into frictional contact with the skin surface on opposite sides of the deformed skin tissue area, said at least two electrodes being movable with respect to each other, said at least two radiofrequency electrodes comprising surface portions providing a high coefficient of friction when in contact with said skin surface, and a thermometer configured to detect a temperature of the skin tissue area and a control unit configured to operate the apparatus as a function of one or more signals from the thermometer, a profilometer configured to:
provide information on a height profile of a skin tissue relief feature,
provide one or more signals as input to the controller configured to operate the apparatus as a function of said one or more signals to thereby adjust a vacuum system,
adjust a treatment depth of skin tissue folds formed in said deformed skin tissue area by adjusting height differences between relative protrusions and depressions in said skin tissue folds, wherein said height difference adjustments are determined from said provided information provided on said height profile of said skin tissue relief feature, and wherein the apparatus is configured for applying, while maintaining the skin tissue area in said deformed shape, a spatially continuous radiofrequency energy flow between the at least two radiofrequency electrodes on opposite sides of the deformed skin tissue area through the deformed skin tissue area, and for releasing the skin tissue area from said deformed shape after application of the spatially continuous radiofrequency energy flow, and wherein the apparatus is configured to release the skin tissue area from said deformed shape, thereby deforming said heated portion into an oscillatory wave-shaped skin tissue zone of heated skin tissue extending at various depths within the skin tissue, wherein a depth variation relative to the skin surface that varies between a minimum depth value and a maximum depth value in a direction between said opposite sides, and crosses a dermal junction, wherein the temperature and spatial extent of the skin tissue zone is related to a power and a duration of the applied RF energy, wherein the minimum depth value is substantially zero and the maximum depth value may be in a range of several millimeters, thus facilitating a fractional RF treatment, and wherein the deformed skin tissue area has an interdistance of 0.1 to 2 cm with respect to a direction generally perpendicular to the folds.

* * * * *